United States Patent [19]

Marquette

[11] Patent Number: 4,793,333
[45] Date of Patent: Dec. 27, 1988

[54] KNEE STABILIZER

[76] Inventor: Stuart H. Marquette, 2927 Via Pepita, Carlsbad, Calif. 92008

[21] Appl. No.: 857,918

[22] Filed: Apr. 30, 1986

Related U.S. Application Data

[63] Continuation-in-part of Ser. No. 732,345, May 8, 1985, abandoned, which is a continuation-in-part of Ser. No. 579,728, Feb. 13, 1984, Pat. No. 4,733,656.

[51] Int. Cl.$^4$ .............................................. A61F 5/00
[52] U.S. Cl. ...................................... 128/80 C; 2/22; 128/80 F
[58] Field of Search .................. 128/80 R, 80 C, 80 F, 128/87 R, 165; 2/22, 24

[56] References Cited

U.S. PATENT DOCUMENTS

| | | | |
|---|---|---|---|
| 1,622,211 | 3/1927 | Sheehan | 128/80 C X |
| 3,387,305 | 6/1968 | Shafer | 2/22 |
| 3,575,166 | 4/1971 | Rosman et al. | 128/80 R |
| 3,581,741 | 6/1971 | Roseman et al. | 128/80 C |
| 4,041,940 | 8/1977 | Frankel et al. | 2/24 X |
| 4,275,716 | 6/1981 | Scott, Jr. | 128/80 C |
| 4,407,276 | 10/1983 | Bledsoe | 128/80 R X |
| 4,487,200 | 12/1984 | Feanny et al. | 128/80 F X |

FOREIGN PATENT DOCUMENTS 3123144 1/1983 Fed. Rep. of Germany ............ 2/24

OTHER PUBLICATIONS

1983 brochure entitled "The Feanny Knee Orthosis TM", 2 pages (no author).
1983 brochure entitled "The Lenox Hill Derotation Brace TM", 3 pages (no author).
1983 brochure entitled "Graphite Knee Stabilizer", 2 pages (no author).
1983 brochure entitled "CAN-AM TM", 2 pages (no author).
1983 brochure entitled "The Poli-Axial Knee Cage Bracing System-Explanation", 4 pages (no author).

Primary Examiner—Charles A. Pearson
Assistant Examiner—Moshe I. Cohen
Attorney, Agent, or Firm—Flehr, Hohbach, Test, Albritton & Herbert

[57] ABSTRACT

A knee brace having an anterior tibial shell and a posterior femural shell which are closely configured to the shape of the leg and are joined by a closed support band. The combination of shells and band provides anterior-posterior, medial-lateral and rotary stability.

9 Claims, 5 Drawing Sheets

FRONT
FIG. 1

SIDE
FIG. 3A

SIDE
FIG. 3B

SIDE
FIG. 4

SIDE
FIG. 2

FRONT
FIG. 5
PRIOR ART

SIDE
FIG. 6
PRIOR ART

FIG. 12 REAR

FIG. 10 SIDE

FIG. 11 FRONT

KNEE STABILIZER

This application is a continuation-in-part of my co-pending United States patent application, Ser. No. 732,345, filed May 8, 1985, now abandoned which is a continuation-in-part of my co-pending United States patent application, Ser. No. 579,728, filed Feb. 13, 1984, now U.S. Pat. No. 4,733,656.

BACKGROUND OF THE INVENTION

This invention relates to orthotics, to supports or stabilizers for joints and, in particular, to a knee brace which serves both preventive and remedial functions in protecting against medial-lateral, anterior-posterior and rotary instabilities.

The knee joint is perhaps the most susceptible to injury of the major articulated joints of the human body, despite the presence of five major ligaments and two menisci which serve to connect and stabilize the tibia and femur. These anatomical structures include the anterior and posterior cruciate ligaments, the medial and lateral collateral ligaments, the posterior capsule ligament and the medial and lateral menisci.

Anatomically, the knee is designed so that specific muscles or muscle groups, not ligaments, absorb the brunt of external or internal forces. That is, a muscle or group of muscles substitutes for each ligament in the knee to absorb force and resstrict motion. As examples, the hamstrings substitute for the anterior cruciate ligament, the quadriceps for the posterior cruciate liagment, and the abductor and adductor groups for the medial and lateral collateral ligments.

The articulation of the knee joint, and the ligaments, muscles and bones associated with the joint are described, for example, in Gray's Anatomy and in The Johns Hopkins Atlas of Human Functional Anatomy, 2d ed., 1980. These publications are incorporated herein by reference.

When a muscle is unable to completely absorb an applied force, either because of inherent weakness or prior injury or simply because the force is too strong, the unabsorbed component of force is transmited to one or more ligaments. If the transmitted component is sufficiently great, the ligament is strained or torn. Ligamental susceptibility to injury is also dependent upon the degree of flexion or extension. The inherent cooperation and relationship among the ligaments is such that when the knee is bent or flexed, some ligaments are relatively tight and tend to control displacement, but others are relatively loose. Between 20°–60° of flexion, the knee is very susceptible to displacement and to injury. This is unfortunate, because the knee is frequently in this position, particularly during the more active sports activities.

It is factors such as these which make the knee relatively weak compared to the other major articulated joints. Some, such as the relatively simple ball and socket hip joint, are very secure. Other, such as the elbow and shoulder joints are complicated but nonetheless relatively secure. Despite its inherent weaknesses, the knee joint must both support the weight of the body and provide for movement, while holding the tibia and femur in position along their substantially planar unstable interface.

In considering external forces applied to the knee and the resulting ligament injuries, it is helpful to simplify the situation somewhat and consider the forces as having their major components applied primarily along a frontal plane through the knee, or along a sagittal plane through the knee, or as comprising a rotatory force. Frontal plane forces are medial-lateral forces which displace the femur and/or tibia in a side-to-side direction. Saggital plane forces are anteriro-posterior forces which displace the femur and tibia in approximately a front-to-back motion, and includes drawering forces applied during flexion or extension. Rotatory forces are those which tend to induce relative rotational displacement of or between the femur and tibia, primarily against the stabilizing force provided by the anterior cruciate ligament.

Figure 1:
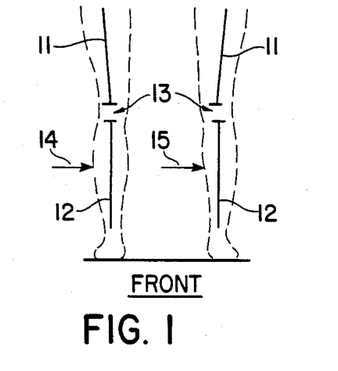
FIG. 1 schematically illustrates the application of medial and lateral forces to the human leg.
Figure 2:
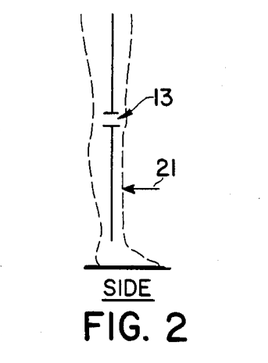
FIG. 2 schematically illustrates the application of a posterior tibial force to the human leg.
Figure 3A:
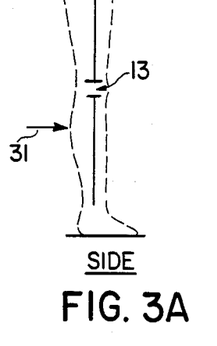
FIGS. 3A and 3B schematically illustrate, respectively, application of an anterior tibial force and an external rotation anterior tibial force to the human leg.
Figure 3B:
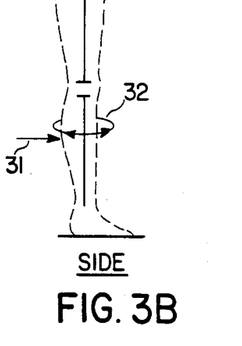

FIGS. 1 through 3 illustrate examples of the above forces. In these schematic drawings, the femur, tibia and knee are respectively designated 11, 12 and 13. Referring specifically to FIG. 1, two of the more common knee ligament injuries result from medial and lateral forces. The lateral collateral ligament and medial collateral ligament are primary stabilizing influences against medial and lateral force, respectively. As a consequence, strains or tears of lateral collateral ligament and the medial collateral ligament tend to result, respectively, from medial forces, that is, inward or medially-directed forces 14 applied aginst the outside of the leg, or lateral forces 15, which are outward directed forces applied against the inside of the leg.

FIG. 2 depicts a posterior force 21, i.e., a rearward-directed force. The knee 13 is stabilized against posterior forces primarily by the posterior cruciate ligament. The posterior cruciate ligament is backed by the posterior capsule ligament, which is quite effective in stabilizing the knee against displacement. As a result, isolated posterior cruciate tears are rare. Usually injuries to other ligaments are also involved. In fact, it is not infrequent that the bone attachment itself tears rather than, or in addition to the posterior capsule ligament.

Figure 4:
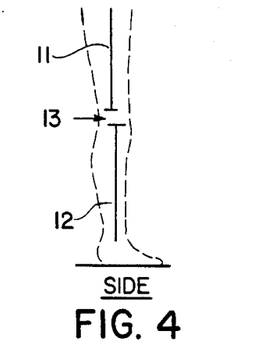
FIG. 4 illustrates the resultant displacement of the tibia relative to the femur.

Perhaps the most frequent injury in sports, and certainly one of the most damaging injuries to the joints involves strains or tears of the anterior cruciate ligament (also termed the "ACL"). Referring to the side view shown in FIG. 3A, the responsible force may involve an anterior tibial force alone, that is, a forward-directed force 31 applied to the back of the tibia. This anterior force an result from a direct blow, such as hyperextension or a fall. As shown in FIG. 3B, the force may involve a rotational tibial force 32 which rotates the tibia relative to the femur (as by catching a ski, or by catching a shoe or cleats in turf) or the combination of a rotatory force with an anterior tibial force 31. The injury is a direct result of excessive force which the substitutional muscles and the anterior cruciate ligament are unable to absorb and a resulting anterior tibial acceleration and displacement relative to the femur. See FIG. 4.

The reason for the frequent occurrence of injuries to the anterior cruciate ligament is two-fold, namely the frequency with which the knee and leg are subjected to large magnitude forces, and the susceptibility to injury such as tearing in that typically the knee can withstand only about 380 pounds of force and 12.5 millimeters displacement or movement between the tibia and the femur without injury to the anterior cruciate ligament. If the knee happens to be flexed at the time the forces are applied, the probability of serious ACL injury becomes even greater. Of course, if there is existing damage or if the anterior cruciate ligament has inherent instability, the knee is more susceptible to displacement and the ligament is more susceptible to injury. The same is true of the other ligaments.

Any effective knee orthosis should be designed to provide three protective functions for the anterior cruciate ligament. First, it should restrict the movement of the tibia, absorbing the anterior force and eliminating any ACL damage or tear before it occurs. Second, it should stabilize the already weak or injured ACL against further injury to itself and, third, it should also provide decreased risk of injury to secondary structures sucha s the medial collateral ligament or the medial meniscus where the ACL is weak or injured. Thus, in addition to preventing an injury initially, effective knee orthosis may permit continued or resumed participation in regular athletic activities where there is an existing injury.

Concentrated efforts by the orthotics profession to develop knee stabilizers are thought to have been initiated in the 1960's as a result of publicized knee injuries suffered by professional athletes. It is believed basically two types of knee braces have dominated this field. Referring to the FIG. 5 front view, one such brace 50 uses a three-point pressure which is provided by two pads 51 and 52 situated above and below the knee (on either the medial or the lateral side of the leg) and a third pad 53 on the opposite side of the leg adjacent the knee. Rigid braces 54-54 connect the pads. Various straps can be used to enhance suspension and/or stabilization characteristics.

Figure 6:
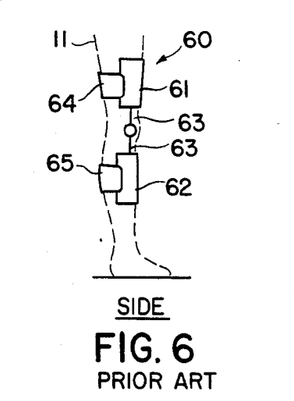

Referring to the side view shown in FIG. 6, the second type 60 of conventional knee brace uses relatively rigid anterior femural and tibial shells 61 and 62 which are joined by hinged uprights 63–63 and are supported in the back or posterior side by elastic straps 64 and 65. These designs are more effective at protecting against medial-lateral forces than anterior-posterior forces. The reason is simple. The rigid shells/pads and connecting braces provide relatively inflexible pressure points which stabilize against lateral or medial forces.

Figure 5:
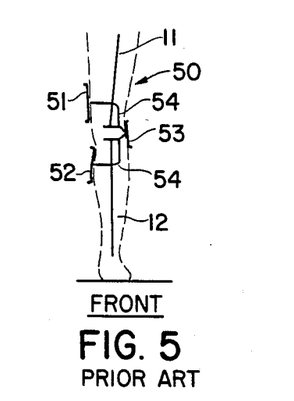
FIGS. 5 and 6 are, respectively, front and side schematic illustrations of two conventional knee braces.

In contrast, the relatively flexible front-to-rear stabilization systems provided by the braces 50 and 60 permit relative movement of the tibia and femur along the sagittal plane.

In addition, because rotary stability is a function of both medial-lateral and anterior-posterior stability, the implementation of conventional knee brace designs tends to be less effective than desired in any derotation function. Furthermore, stabilization in all aspects is closely related to the effective suspension of the orthotic device on the knee and leg in a manner such that the device does not alter or shift its position on the leg as by planing. Many prior art devices experience planing and shifting which detract from their ability to provide medial-lateral stability, anterior-posterior stability and/or rotatory stability.

Frequently, designers of prior art knee braces have attempted to avoid the problems associated with flexion as well as suspension and stability by simply encasing the knee or leg in a rigid, heavy brace, using considerable strapping, which restricts movement of the knee. Because of restrictions on movement and because of weight, such braces put the athlete at such a competitive disadvantage that these knee braces are not widely used for injury prevention. Rather, the primary use has been compensatory or remedial, that is, to compensate or stabilize knees with one or more weak or injured ligaments (such as the anterior cruciate ligament) and to prevent injury to other structures in knees in which ligaments are already torn or attenuated. Perhaps the only exceptions to the use of prior art knee braces for remedial purposes rather than prevention are the braces depicted in FIGS. 5 and 6, as well as the class of braces which consist simply of a pair of upright bands on the sides of the leg. However, this latter type of brace is used to provide some means of protection against medial-lateral forces, not anterior-posterior forces and, as mentioned above, the former two types are not wholly effective in protecting against injuries to the anterior cruciate ligament.

In short, a knee orthosis can serve any of three crucial purposes related to the anterior cruciate ligament: to prevent anterior cruciate ligament injury, to stabilize a knee having a weak or injured anterior cruciate ligament, and to prevent further injury to secondary structures when the anterior cruciate ligament has already been torn or attenuated. However, as discussed above, because of (1) the large forces which are applied to and generated by the leg and (2) the very small displacement which is possible without injury to the anterior cruciate ligament, it has proven very difficult to accomplish these goals of stabilization and, in particular, of prevention. Furthermore, the requirements of light weight and comfort and freedom of movement are, seemingly, in direct conflict with the goals of suspending the brace on the leg without relative movement relative to the leg and restricting the displacement of the anterior cruciate ligament. Probably because of these conflicting requirements, with the exception of the braces disclosed in my above two copending applications, known braces are believed to be designed to provide light weight and freedom of movement at the expense of adequately stabilizing the knee, or to rigidly encase the knee at the expense of light weight and freedom of movement.

SUMMARY OF THE INVENTION

In view of the above discussion, it is one object of the present invention to provide a new and improved knee brace suspension system which restricts planing and other movement of the knee brace relative to the leg and knee.

It is another object of the present invention to provide a new and improved knee brace which protects against displacement and injuries to the anterior cruciate ligament.

It is another object of the present invention to provide a new and improvded knee brace which protects against displacement and medial-lateral, anterior-posterior and rotary instabilities.

Another object, related to the above objects, is to provide a knee brace which simulates the function of the anterior cruciate ligament.

It is also a related object to provide a knee brace which, when rotational and/or anterior forces are applied to the tibia, absorbs a large part of the anterior component and restricts anterior movement of the tibia to no more than a few millimeters and, as tibial movement is restricted, transfers the absorbed force to the distal posterior femur, thereby approximating the normal function of the anterior cruciate ligament.

It is also an object, in effecting such absorption and transfer of force, to compensate for the large mass of soft tissue which surrounds the femur and makes the effective absorption and transfer of force difficult, and to provide absorption and transfer without inhibiting the movement or function of the hamstring muscles.

It is still another related object of the present invention to provide a knee brace which absorbs and counters the anterior force on the tibia resulting from the contraction of the quadricep muscles during flexion of the knee.

Another object of the present invention is to provide a knee brace which counters inertial force generated by its own weight at the terminal point of the swing phase, and which limits extension of the leg to less than 180°.

Finally, but not exhaustively, it is an object of the present invention to provide a knee brace which is comfortable, non-restrictive, and relatively light weight.

In a presently preferred embodiment, the knee stabilizer of the present invention comprises (a) a closed band system, (b) a relative rigid anterior tibial shell and (c) a relatively rigid posterior femoral shell. Element (a), the closed band system, surrounds the leg and thigh of a wearer, and itself comprises a pair of medial and lateral femural uprights, a transverse posterior band connecting between the pair of femural uprights, a pair of medial and lateral tibial uprights, a transverse anterior band connecting between the pair of tibial uprights, and joint means pivotally connecting the two pair of uprights. Element (b), the anterior tibial shell, comprises an anterior section which is mounted to the transverse tibial band adjacent the knee and thereby defines a first pressure point. The anterior section is connected between a medial section and a lateral section of the shell which are mounted, respectively, to the medial tibia upright and the lateral upright. The medial and lateral sections define a posterior opening therebetween. The tibial shell also comprises strap means for spanning the posterior opening to cinch the shell against the wearer's leg. As a result of this overall construction, the tibial shell absorbs anterior tibial force components at the first pressure point and transmits the force via the tibial uprights to the femural uprights. Element (c), the posterior femoral shell, comprises a posterior section mounted to the transverse femural band proximate the knee and thereby defines a second pressure point. The posterior section is connected between a medial section of the femural shell and a lateral section thereof. The medial and lateral sections are mounted, respectvely, to the medial femur upright and the lateral femur upright and define an anterior opening. The femural shell also comprises strap means spanning the upper anterior opening for cinching the femural shell to the wearer's thigh such that the force transmitted to the femur uprights is transmitted via the second pressure point to the femur.

The pair of femural uprights define a lever pivotally positioned on the thigh at a fulcrum defined by the transverse femural band such that cinching the femural shell pivots the upper end of the lever anteriorly about the fulcrum, thereby producing a rearwardly-directed counterforce at the lower end of the lever for counteracting anterior tibial force components.

In another relative aspect, preferably the posterior section of the femural shell comprises two protruding relief sections and an intervening recession closely approximating the outline of the biceps femoris tendons and the semitendenosis tendons and the intervening soft tissue above the back of the knee. Cinching the femur strap means pre-compresses the soft tissue against the femur for efficiently transmitting the anterior tibial force component from the second pressure point through the compressed soft tissue to the femur.

Preferably, the femur strap means comprises an anterior quadriceps pad shaped for fitting within the anterior opening of the posterior femural shell and against the quadriceps muscles for facilitating cinching of the femural shell to the wearer's thigh.

DETAILED DESCRIPTION OF THE INVENTION

Purposes and Objectives

As mentioned above, a knee orthosis should serve three purposes with respect to the anterior cruciate ligament: to prevent injury to the anterior cruciate ligament, to stabilize a knee having a weak or injured anterior cruciate ligament, and to prevent further injury to secondary structures when the anterior cruciate ligament has been torn or attenuated.

As the result of my research and development efforts, and discoveries made during these efforts toward adopting the knee brace to best serve the above three purposes, it is believed achieving these purposes is contingent upon satisfying the following three major anatomical objectives:

First, the orthosis or knee brace must approximate and supplement the normal operation of the anterior cruciate ligament in restricting anterior movement. The anterior/posterior component is the crucial component of rotatory forces. When rotational and/or anterior forces are applied to the tibia, the orthosis should absorb a large part of the anterior component and restrict movement to no more than a few millimeters. That is, the orthosis should approximate and supplement the action of the anterior cruciate ligament in this respect. (If the orthosis allows the knee joints to begin moving further, the possibility of stabilizing the tibia is lost.) Then, as tibial movement is restricted, the orthosis should transfer the absorbed force to the distal posterior femur, again approximating and supplementing the normal function of the anterior cruciate ligament.

In addition to the inherent difficulty in approximating/replicating the action of the anterior cruciate ligament in an external orthosis, there are two other complicating anatomical factors that must also be considered: (a) the femur is surrounded by a large mass of soft tissue, making effective transfer of force difficult; and (b) the force must be absorbed and transferred in such a way that it does not inhibit the movement or function of the hamstring muscles.

Secondly, the orthosis should counter the anterior tibial force generated by flexing of the quadriceps muscles. When the leg is in motion, the knee is stabilized in flexion by the four quadriceps muscles. Expansion of the quadriceps applies an internally-generated anterior force on the tibia which is precisely the same type of force the orthosis must restrict. The orthosis must effectively absorb or counter this additional anterior tibial force.

Third, the orthosis must be comfortable and non-restrictive. For example, a comfortable orthosis enables an athlete to perform longer and better, and to concentrate more fully on the activity at hand and less on the presence of the orthosis. Athletes who cannot reach a comparable level of activity because of a restrictive orthosis may eventually become frustrated into inactivity or into foregoing the protection of a knee brace.

Finally, in addition to these three major objectives, an orthosis should counter inertial force generated by its own weight at the terminal point of the leg's swing and should limit leg extension to less than 180°.

My knee brace, which is depicted in FIGS. 7 through 18, is designed to accomplish the above objectives and thereby serve the three anterior cruciate ligament injury prevention and stabilization purposes and to provide medial-lateral and rotary stabilization.

Five Pressure-Point Brace 70

Figure 7:
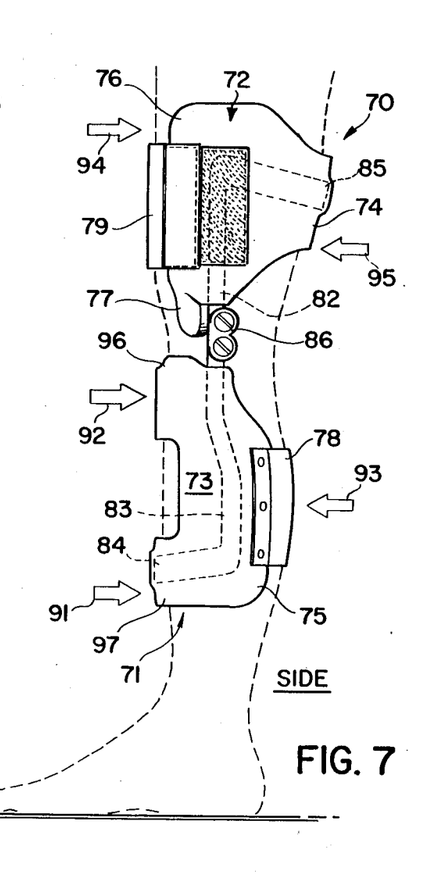
FIGS. 7, 8 and 9 are, respectively, side, front and rear elevation views of a five pressure-point embodiment of the knee stabilizer of the present invention, including, in FIG. 7, illustration of the positioning of the knee stabilizer on the human leg.
Figure 8:
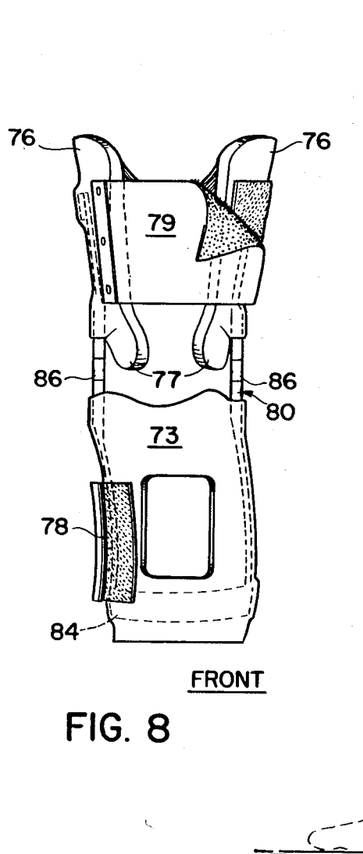
Figure 9:
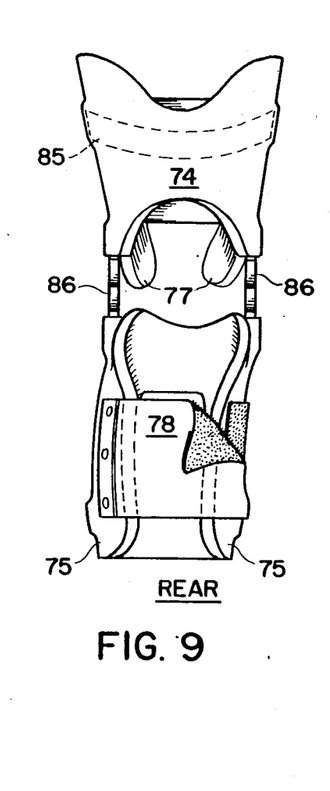

A five pressure-point embodiment 70 of the knee stabilizer of the present invention is shown in FIGS. 7, 8 and 9. The knee stabilizer 70 comprises a tibial shell 71, a femural shell 72 and a closed band structure 80 which joins the two shells and includes a joint 86 on either side of the knee for substantially tracking flexion of the knee. The shells and band are carefully tailored and configured to conform to the shape and size of the individual leg and knee. The tibial shell 71 includes upper and lower borders or sections 96 and 97 which span the anterior (front) side thereof and which, particularly in applications requiring light weight, may be open at the posterior (rear) side. The phrase "anterior tibial shell" as used herein thus refers to tibial shell 71 having one or more sections which span the anterior or front side of the lower leg. Similarly, the femural shell 72 is closely configured to the size and shape of the thigh, and has a support section 74 which spans the posterior or rear side of the thigh. Thus, as used here, the phrase "posterior femural shell" refers to a femural shell 72 which has a section 74 spanning the posterior side of the thigh. In addition, the tibial shell 71 has sections 75—75 which partially wrap around the medial and lateral posterior sides of the leg and the femural shell 72 has sections 76—76 which wrap partially around the medial and lateral anterior sides of the femur. One purpose of these partial sections is to enhance the suspension characteristics of the leg; at the same time, the openings defined between sections 75—75 and between sections 76—76 contribute to the light weight and ease of application of the stabilizer 70.

The anterior sections 76—76 of the femural shell each include a stabilization or suspension tab 77 which is configured to and positioned between the patella or knee cap and the femural epicondyle located on that side of the knee. The tibial and femural shells have straps 78 and 79 respectively attached thereto for spanning their respective posterior and anterior openings to aid the suspension of the shells on the leg and thigh.

Typically the straps 78 and 79 are rigidly attached along one side, as by metal rivets, and are releasably attached on the opposite side, as by Velcro ™ hook and loop type fasteners, to permit releasing the straps to fit the knee stabilizer onto the leg and to provide an adjustable snug fit of the knee stabilizer 70 onto the leg.

Referring in particular to FIG. 7, the tibial end femural shells 71 and 72 are rigidly suspended relative to one another and the knee by the band suspension system 80. This system comprises metal bands which are configured to the outline of the shells and leg. The system includes a pair of substantially vertical uprights 82—82 attached to the medial and lateral sides of the femural shell 72 and, similarly, a pair of substantially vertical uprights 83—83 attached to the medial and lateral sides of the tibial shell 71. A tibial band 84 is attached to the uprights 83—83 on opposite sides of the tibial shell 71 and spans the closed anterior section of the shell. Similarly, a femural band 85 is attached to the uprights 82—82 on opposite sides of the femural shell and spans the posterior side of the femural shell. The uprights 82 and 83 are joined proximate the knee by a conventional polycentric knee joint 86 which is designed to pivot in a curve which tracks the knee, i.e., is similar to the anatomical movement of the knee.

The knee stabilizer 70 includes several advantageous suspension features. It should be noted that the word "suspension" refers to retaining a knee brace on the knee and leg without movement of the brace relative to the knee or sliding downward toward or onto the knee. Suspension, of course, contributes to the ability of the brace to stabilize the knee and leg and many of the factors which are necessary for adequate suspension also contribute to stabilization. That is, improving suspension improves stabilization. One advantageous feature of stabilizer 70 is the custom-tailored contour of the shells 71 and 72 and band system 80. In being precisely configured to the shape of the leg and thigh, both at the anterior and posterior sides as well as the medial and lateral sides, a secure fit is provided and movement of the stabilizer relative to the leg is inhibited. A second, related aspect is that the closely configured shells of the stabilizer 70 also encompass or cover more of the perimeter of the leg and thigh than most conventional braces. Third, the rigid band support system 80 comprises a unitary configuration which tracks the primary stress points (the back of the thigh, the front of the tibia, and the sides of the legs), and thereby keeps the configured shells firmly in place on the leg and contributes to excellent stability. Also, as mentioned above, the polycentric knee joints 86—86 track in a curve much the same as does the knee, which facilitates maintaining the shells in position during flexion and extension of the knee.

In addition, the brace incorporates a circumferential perimeter differential. That is, the distal border (lower portion) of the femoral shell 72 has a smaller circumference than the adjacent underlying femoral condyles. This is done by applying pressure anterior to the adductor epicondyles on the medial side of the femoral condyles and anterior to the ilio tibial band on the lateral side. A related feature is the suspension tabs 77—77 which are discussed below. Among other advantages, an auxiliary strap can be used to connect the superior border of the tibial shell to provide additional stabilization against inertia in unusually high stress situations.

In considering the stabilization and suspension characteristics of the knee stabilizer 70, refer initially to the front and rear depictions of FIGS. 8 and 9, as well as the side view of FIG. 7. In contrast to prior art braces, the stabilizer 70 stabilizes against medial-lateral forces very well, in part because the shells 71 and 72 circumferentially encompass more of the critical regions of the leg than prior art braces, with a reduced coverage of non-essential areas. The shells fully cover both the lateral and medial sides of the thigh and leg proximate the knee. Displacement side-to-side is further constrained by the closed anterior section of the tibial shell 71, the partial wraparound of the posterior section 75 of the tibial shell, the closed posterior section of the femural shell 72 and the partial wraparound of the anterior section 76 of the femural shell, in conjunction with the additional constraint against side-to-side displacement provided by the closed configuration of band 80, that is the posterior femural band 85, the anterior tibial band 84 and the interconnecting uprights 82 and 83. In contrast to the three-point medial-lateral stabilization of many prior art braces, the described construction of the knee stabilizer 70 provides essentially continuous support and stabilization against displacement from the lower or distal edge of the tibial shell 71 to the upper or superior edge of the femoral shell 72.

Those skilled in the art will appreciate that the above-described structural features which provide medial-lateral stability also contribute to anterior-posterior stability. The structure of the knee stabilizer 70 incorporates key pressure points which are designed to protect against anterior-posterior instability as well as medial-lateral and rotary instability. Referring to FIG. 7, five of these points are indicated generally by the arrows designated 91-95. These incude three pressure points or regions which securely lock the tibia: the distal (lower) 91 and proximal (upper 92) borders of the closed anterior tibial shell section 73, and the vertically intermediate posterior point 93 defined by the posterior section and elastic strap 78 of the tibal shell; and two femural pressure points: the anterior proximal (superior) femural border 94 and the posterior distal border 95 of the closed posterior section 74 of the femoral shell.

Those skilled in the art will quickly appreciate that the other structural features such as tabs 77—77 also serve important stabilization functions.

The effectiveness of this suspension and pressure system design can be illustrated by considering application of the anterior tibial force 21 shown in FIG. 2A and the external rotation anterior tibial force 21-22 shown in FIG. 2B. As indicated previously, these are frequently responsible for injury to the anterior cruciate ligament, perhaps the most frequency injury in sports. In response to an anterior tibial force 21 of sufficient magnitude, the tendency is for the lower leg 12 to move and potentially injure the anterior cruciate ligament. However, this movement transmits pressure against the closed borders 96 and 97 of the anterior section 73 of the tibial shell 71 and and is absorbed by the tibial shell. This absorbed force is in turn transmitted via the band support system 80 and femur band 85 thereof to the femural shell 72. The closed posterior section 74 and, in particular, the distal border pressure point 95 transmit any displacement of the lower leg into like displacement of the thigh and thereby prevent displacement of the tibia 12 relative to the femur 11. In short, the anterior-directed tibial force 21 is transmitted as an anterior-directed femural force to stabilize the femur and tibia and prevent relative displacement.

Considering now the rotational component 22 of the exterior force, one will recall that the tendency of prior art braces is to rotate on the leg. In the knee stabilizer 70, an additional stabilizing influence to those previously described is provided by the stabilizing pads 77—77 which provide pressure at the distal border of the anterior femural shell section 76. In response to such rotational forces (either or both anterior-lateral or anterior-medial), one of the pads 77 is constrained from movement by the opposite epicondyle, while the other pad is constrained by the patella. As a result, the anterior cruciate ligament is stabilized agaist movement, along with the other knee ligaments and the entire knee. In addition, reduction of anterior motion reduces rotational instability.

In working embodiments of the knee stabilizer 70 designed for a six foot, 180 pound male, the overall length of the stabilizer was 19.5 inches. The femural shell was polyproplyene plastic three-sixteenths of an inch thick while the tibial shell was one-eighth inch thick polyproplene. The shells were lined with one-quarter inch thick medium density aliplast. The bands and uprights were both made of 2024 aluminum alloy to provide light weight and strength. The bands ranged from one-eighth by three-quarters inch to one-eighth by one and one-half inch, depending upon the patient's size and activities, while the uprights were one-eighth by three-quarters of an inch. The joints were Becker 1009B aluminum polycentric knee joints, formed by machining to provide enhanced smoothness and tracking. The joints limit extension of the leg to $\leq 180°$. Silver solder can be inserted into the joint gear to limit flexion to a prescribed range. The straps 78 and 79 were gum rubber reinforced by leather at the Velcro and Dacron at the copper rivet attachment points. The resulting stabilizer weighed 24-40 ounces and provided excellent movement and mobility.

Four Pressure-Point Brace 170

Figure 10:
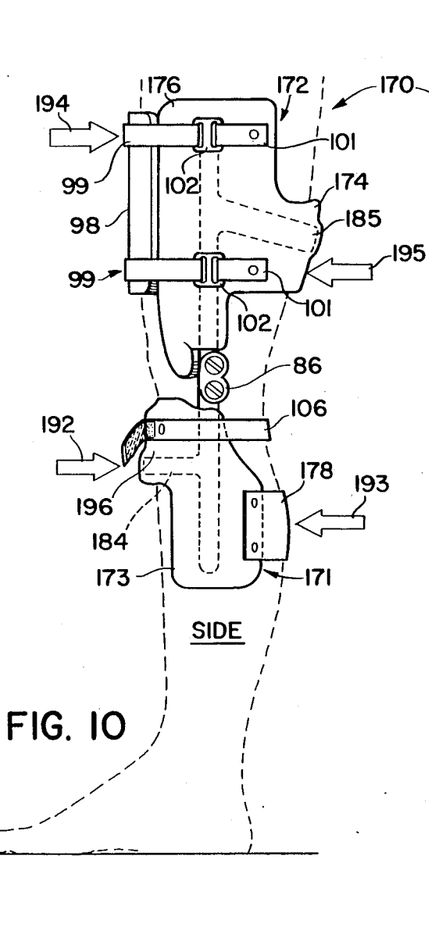
FIGS. 10, 11 and 12 are, respectively, side, front and rear elevation views, in the manner of FIGS. 7, 8 and 9, illustrating a light weight, four pressure-point version of my knee stabilizer.
Figure 11:
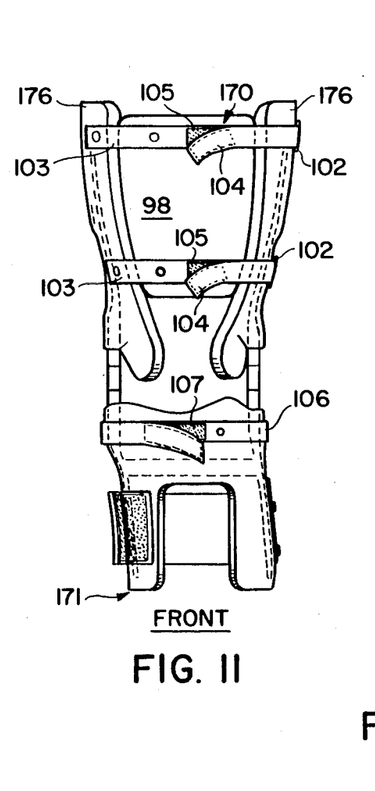
Figure 12:
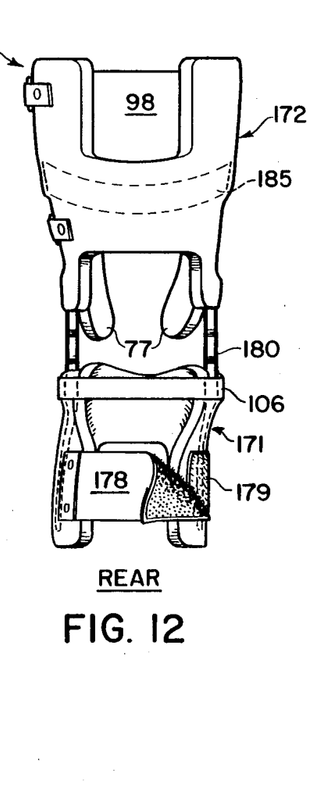

A second embodiment 170 of my knee bracke is illustrated in FIGS. 10-12. Specifically, the stabilizer or brace 170 is a four pressure-point system, a three point pressure system with a fourth inertial control strap. In describing the four pressure-point brace 170, components which correspond to components of the five pressure-point brace 70 illustraed in FIGS. 7-9 are identified by the same numbers such as 86, 99, 93; components which are modified versions of components such as those numbered 70-74, 76-79, 80, 82-85, 94-96 are identified by adding the prefix "1" to the numbers: 170-174, 176-179, 180, 182-185 and 194-196. Thus, for example, the modified tibial shell 171 of the four point pressure brace 170 corresponds to the tibial shell 71 of the five point pressure brace 70.

The femural shell 172 of the four pressure-point brace 170 includes elongated medial and lateral sections 176—176 which extend farther up the thigh than do the corresponding components 76—76 of brace 70, FIG. 7. Anterior strap 79 is omitted. In its place is provided a typically elongaged free-floating anterior quadriceps pad or plate 98 which is positioned bewteen the elongated medial and lateral upright sections 176—176. The anterior quadriceps pad 98 typically is mounted to the femural shell 172 by a pair of straps or belts 99—99. The belts 99—99 can be single-piece continuous straps which are fastened by buckles, Velcro TM loop and hook-type fastening material, etc.

In the illustrated embodiment, each belt 99 includes a strap or belt section 101 which is riveted at one end to one upright section 176 of the femural shell an mounts a buckle 102 at the loose end. A second strap or belt section 103 is attached by rivets to the other upright section 176 of the femural shell 172. The belt section 103 also extends across, and is riveted to, the free-floating anterior quadriceps pad 98, and is of sufficient length to permit looping of its end 104 through the buckle 102 to provide an adjustable, loop-back fastening or closing of the belt 99. Typically, each belt 99 is adjustably fastened by, for example, mating lengths of Velcro TM or other hook and loop-type fastening material 105 which are attached to the outer-facing surface of the inner portion of the belt section 103 and to the inner-facing surface of the overlapping end 104 of the belt section 103. The belts 99 preferably are formed of inelastic material such as Dacron material. An inelastic or fixed system provides better anterior pressure on the quadricep muscle and also transfers force better than an elastic system. As a result, the femural pressure point at 194 is improved. The other, second femural pressure point 195 is provided by the posterior border 174 of the femural shell 172 and the associated posterior femural band 185 corresponding to the pressure point 95 of the five pressure-point shell 70.

Referring further to FIGS. 10-12, the tibial shell 171 of the four pressure-point brace is shorter, smaller and therefore of lighter weight than the tibial shell 71, FIGS. 7-9. The tibial shell 171 provides two pressure points (the third and fourth system pressure points), rather than the three points of the alternative five pressure-point embodiment 70. The narrower elastic band or strap 178 which spans the posterior opening of the tibial shell 171 is attached at one end to the shell 171 by rivets and is releasably attached at the other end to fastener 179, as by mating Velcro TM hook and loop-type fastening surfaces. The adjustable strap 178 provides the third pressure point of the system. The fourth pressure point of the brace is provided at the superior anterior band 196 of the tibial shell 171.

To decrease weight, the lower anterior band 97 of the five pressure-point brace 170 (FIG. 7) is omitted and, as a consequence, the lower ends of the medial and lateral upright shell sections 173—173 terminate in the open configuration which is shown most clearly in FIG. 11.

In addition, the anterior tibial band 184 of the band pressure system is positioned at the superior band or border 196 to enhance the rigidity and support at the fourth pressure point 192.

Suspension of the tibial shell 171 on the leg is further enhanced by a circumferential strap or belt 106 which spans the circumference of the leg at the superior border of the tibial shell. While various constructions and means of attaching the belt 106 are possible and in fact, while it need not be attached to the tibial shell 171, the belt 106 typically is attached to the tibial shell 171 by rivets and is closed by using lengths of Velcro TM fasteners 107 which are attached to the outer-facing surface of the belt and to the inner-facing surface of the overlapping end of the belt.

In summary, in the four-pressure-point brace 170, the lower anterior band 97 of the tibial shell is eliminated and the metal strut 84 of the band system is moved vertially, to 184, and is incorporated into the upper anterior section 196 of the tibial shell. The posterior elastic band 178 of the tibial shell is narrower than band 78. Also, the anterior elastic band 79 of the femural shell has been replaced by an inelastic fixed-strap system which incorporates belt(s) 99 and the anterior quadriceps pressure pad 98.

Referring speficially to FIG. 10, in addition to lighter weight, this alternative brace construction 170 provides an improved pressure system. As mentioned, the four point-pressure system is effectively as three point-pressure system with a fourth, inertial control strap, the posterior tibial strap 178. The four pressure points are first, the distal posterior femural point 195; second, the vertically upwardly spaced anterior femural point 194; third, the distal posterior tibial point 193; and fourth, the vertically upwardly spaced superior anterior tibial point 192. The objective of the system is to apply force at anterior tibial point 192, using the brace and its band system as a lever system and the posterior femural point 195 as the fulcrum. Pressure is applied at the anterior femural point 194 by the adjustable strap system 99. That is, when pressure is increased at point 194 by tightening the belts 99, the femural section of the band system is pulled anteriorly. This force is transmitted through the fulcrum at 195 and therefore pivots the tibial section of the band system, along with the knee joints and the band section 196, posteriorly. As a result, tightening at one point, using belts 99, securely suspends the knee stabilizer 170 on the leg and provides an optimum combination of light weight and anterior-posterior, medial-lateral and rotary stability.

In a working embodiment of the knee stabilizer 170, designed for a six foot, 180 pound male, the overall length of the stabilizer was 19.5 inches. Both the femural shell and the tibial shell were one-eighth inch thick polypropylene plastic. The shells were lined with one-eighth inch thick medium density aliplast. The bands and uprights were both made of 2024 aluminum alloy to provide light weight and strength. The bands measured one-eighth inch by three-quarters of an inch, while the uprights were one-half inch by one-eighth inch. The pivotal joints of the band system were Becker 1009C aluminum polycentric knee joints, formed by machining to provide enhanced smoothness and tracking. Like the previously mentioned 1009B joints, these joints limit extension of the leg to $\leq 180°$ and can be set to limit flexion to a prescribed range. The posterior tibial strap was gum rubber reinforced by leather at the Velcro and by Dacron at the Speedy rivet attachment points. The anterior femural pressure plate was also formed of one-eighth inch thick polypropylene and the Dacron attachment straps were riveted to the plate and to the femural shell by Speedy rivets. The resulting knee stabilizer weighed between 14 and 24 ounces, depending upon the size and girth of the patient and the patient's activities, and provided excellent movement, mobility and stability.

Pre-stressed Tissue Compression Brace 270

FIGS. 13 through 18 depict a presently preferred embodiment 270 of my knee brace which incorporates the four point suspension and the lever arm action of brace 170, along with pre-cocking and soft tissue compression features. This combination of structural and functional features permits the brace 270 to achieve the above three primary objectives and to thereby accomplish the critical prevention and stabilization functions. The brace 270 meets and exceeds the requirements for an effective knee orthosis through a unique system of adjustable strap, rigid joints and precise casting techniques.

In discussing the brace 270, modified components which are substantially similar to the components numbered xx of brace 70 or 1xx of brace 170 are designated 2xx. Thus, anterior tibial shell 271 is a modified (elongated) version of shell 171 and posterior femural shell 272 is a modified (also elongated) version of 172.

Figure 13:
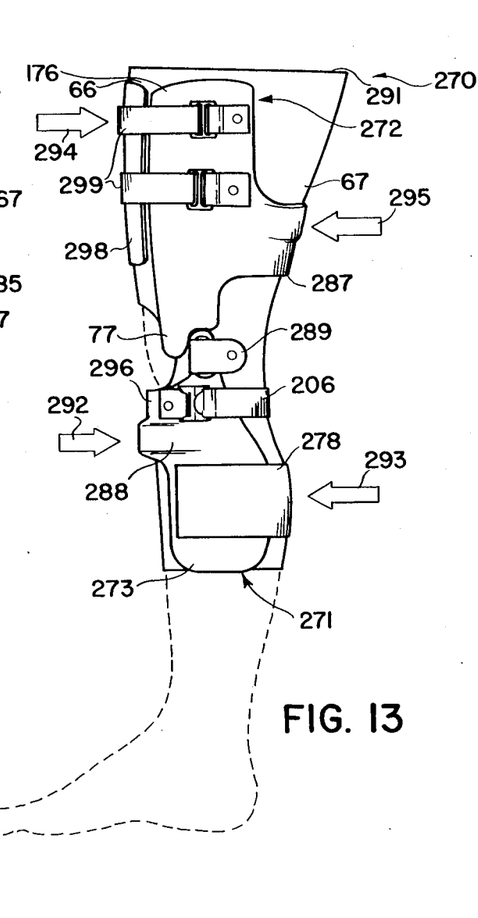
FIGS. 13, 14 and 15 are, respectively, side, front and rear elevation views, in the manner of FIGS. 10, 11 and 12, illustrating a pre-cocked, soft tissue compression, light weight, four pressure-point embodiment of my knee stabilizer.
Figures 14, 16:
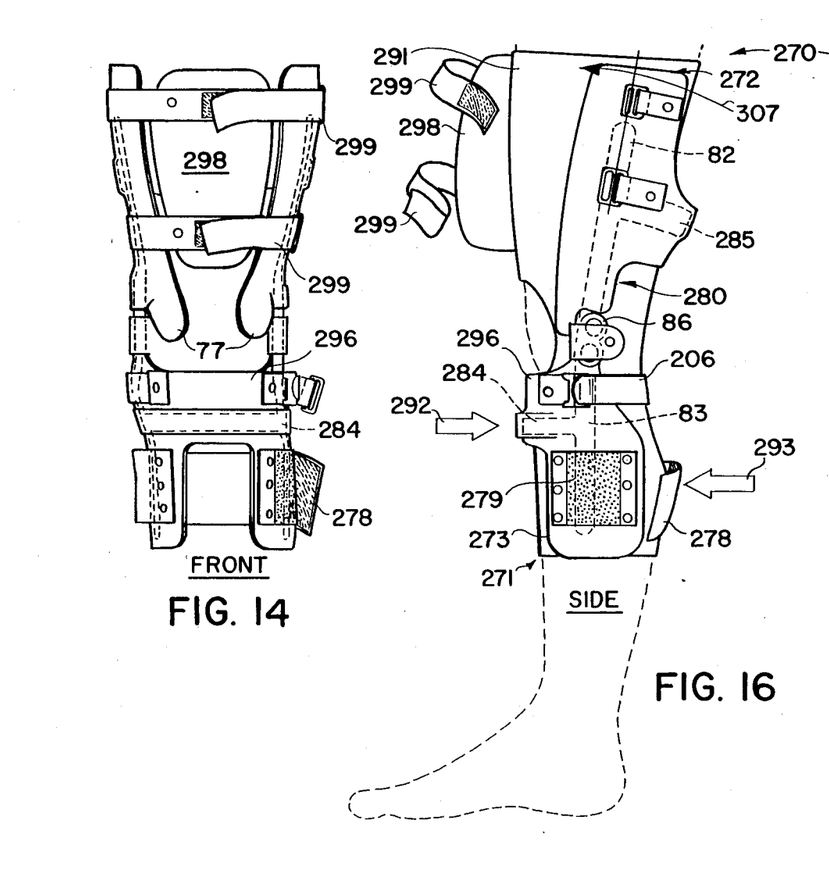
FIG. 16 is a side elevation view, in the manner of FIG. 13, illustrating fitting of the knee brace of FIG. 13 onto the leg of a wearer.
Figure 15:
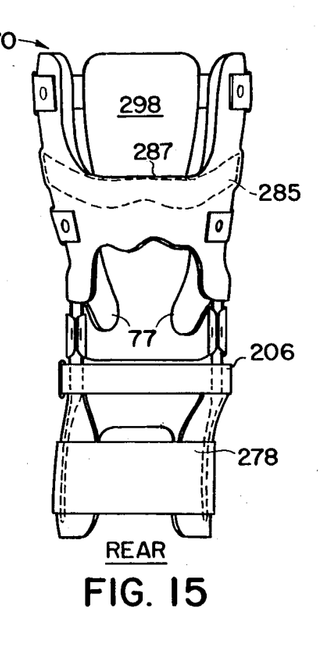

Referring to FIGS. 13 or 16, the basic structure of the brace 270 corresponds to that of brace 70 and, in particular, to that of brace 170. That is, brace 270 includes a relatively short anterior tibial shell 271 and a relatively longer posterior femural shell 272. Both shells are mounted on a closed rigid band structure 280, which includes femural upright 82, tibial upright 83, superior anterior tibial band 284 adjacent the knee and distal posterior femural band 285 which is also close to the knee. Posterior tibial strap 278 defines a posterior pressure point 293. Superior anterior shell section 296 and the associated superior anterior band 284 define an anterior tibial pressure point 292 which is spaced vertically upward from the point 293. Also, the distal border 287 of the femural shell and the associated distal band 285 define a posterior femural pressure point 295 (FIG. 13), and the anterior quadriceps pad 298 and the associated rigid straps 299 define a superior anterior femural pressure point 294 (FIG. 13) which is spaced vertically upward from the femural pressure point 295.

It should be noted that the reference to "first", "second", through "fifth" pressure point is arbitrary in that convenience in discussing the different embodiments 70, 170 and 270 and, in particular, convenience in specifying claim language may require that the same pressure point be designated first, second, etc., at different locations here.

Consider now the three primary objectives of the brace 270 regarding stabilization of and prevention of injuries to the anterior cruciate ligament. First, brace 270 restricts anterior tibial movement through the application of direct pressure by the anterior tibial shell 271 at the superior anterior tibia. The anterior tibial shell 271 is held in place by the adjustable superior posterior strap 206 and the wide posterior elastic band 278 that spans the gastrocnemius (calf) muscle and adjustable attaches to fastener 279. When the knee straps/bands are adjusted to the correct pressure, the shell 271 effectively absorbs anterior tibial force. As the force is absorbed, it is transferred upward by the bands 83 and 82 through the joints to the femural shell 272 and to the distal posterior femur, closely replicating the function of a normal anterior cruciate ligament. As discussed more fully below, the close fit and the size of the upper shell 272 promote the effective transfer of force through the soft tissue 67 (FIG. 13) at the rear of the femur without inhibiting the hamstring muscles.

Figure 17:
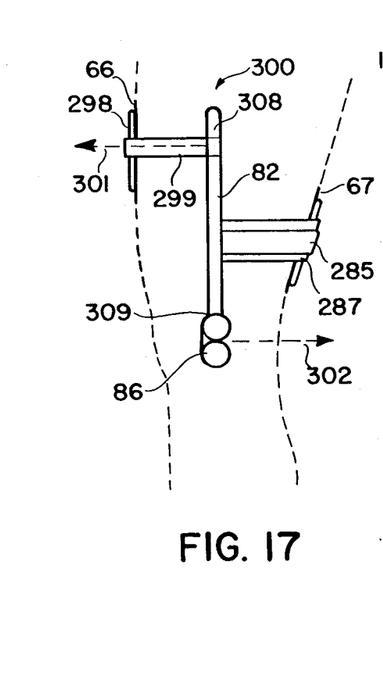
FIG. 17 is a schematic illustration of the lever arm function which is provided by the structure of the knee brace of FIG. 13.

Second, the brace 270 counters internal tibial forces generated by quadriceps flexion with the lever arm system 300, FIG. 17, which is designed into the upper shell and the free-floating pad 298 which rests on the quadriceps muscles in front of the femur. As these muscles flex, they expand, exerting anterior pressure on the pad 298 and creating a posterior force 302 (FIG. 17) on the back of the shell through the lever arm system. This force 302 in turn is transferred directly to the lower shell 271 through the rigid joints 82-86-83, effectively containing the additional anterior tibial force which is generated internally by the quadriceps muscles. The lever arm system 300 designed into the upper shell also serves to control and to stabilize the initial upward transfer of an anterior tibial force from tibia to femur.

Referring generally to FIGS. 13 through 18, the difficulty to effective force transfer which is presented by the large mass of soft tissue surrounding the femur and, in particular, by the mass of soft tissue 67 (FIG. 13) at the rear of the femur, is overcome by the anatomically close fit of the distal posterior border 287 of the femural shell 272 and by the use of the lever arm system to "pre-cock" or pre-stress the brace onto the leg. These features cooperate to compress the soft tissue 67 between the border 287 and the femur.

Figure 18:
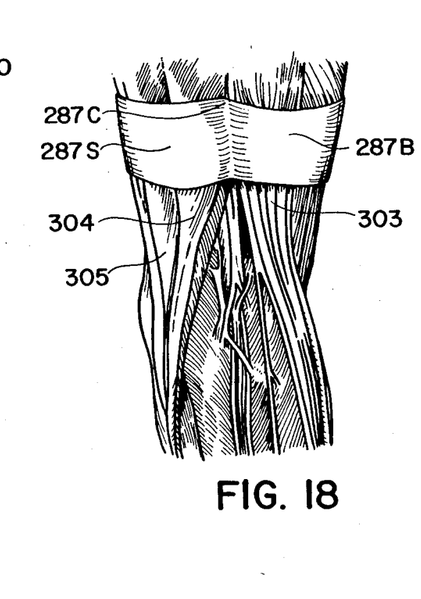
FIG. 18 schematically illustrates the conformal distal posterior border of the femural shell relative to the biceps femoris and semitendenosis muscles and tendons.

Regarding the close anatomical fit, and referring to FIG. 18, the distal posterior band or border 287 of the upper shell 272 preferably is about three inches wide from top to bottom and is conformed to the contour of the hamstring muscles. The border disperses force over a large surface area and includes a shallow central depression 287C, FIG. 18, which corresponds to the space between the biceps femoris tendon 303 and the semitendenosis tendon 304 and applies pressure to the muscle bellies. The depression is flanked by slight bulges or reliefs 287B and 287S corresponding to the location of the tendons of these two respective mucles. The conformed shape and the relief permit compression of the soft tissue without loss of comfort or loss of function. That is, pressure can be applied to the bellies of the hamstring muscles without restricting motion of the biceps femoris and semitendenosis tendons.

Referring to the schematic diagram shown in FIG. 17, a mechanical lever arm system 300 is incorporated into the femural shell 272. The uprights 82 define a lever and the distal posterior femural band 285 and the posterior distal border 287 form the fulcrum of the lever. The lever arm system 300 is used to pre-stress or pre-cock the conformal distal posterior border 287 against the soft tissue 67 at the rear of the thich and thereby compress the soft tissue against the hamstring muscles as the brace is strapped onto the wearer's leg.

Referring to FIG. 16, to fit the brace onto the leg, first, the anterior tibial shell 271 is tightened by cinching the upper posterior strap 206 and the wide elastic band 278. Then, the front femural straps 299 are tightened, pivoting the shell forward, as shown by arrow 307 in FIG. 16, into the locked position shown in FIG. 13.

As the result of the lever arm construction, when the straps 199 are tightened, the pad 298 is forced against the quadriceps muscles so that the femural shell 272 is itself pivoted forward along path 307, FIG. 13, by the resulting anterior or forward directed force 301 which is applied to the upper end 308 of the lever arm. This force 301 pivots the lower end 309 posteriorly or rearwardly about the fulcrum 287. This anterior force 301 also forces the posterior distal border 287 against the soft tissue 67, FIG. 13, compressing that tissue between the border 287 and the femur. As a result, when an anterior tibial force component 31, FIG. 3, is applied to the leg, the force is transferred from the superior anterior section 296 of the lower shell 271 through the rigid band system 280 and is efficiently transferred through the previously compressed (pre-compressed) soft tissue 67 to the femur without being absorbed by this tissue, thereby providing effective transfer of the force and displacement of the femur which closely and efficiently replicates the anterior displacement of the tibia.

The brace is designed so that the lever's fulcrum is typically positioned approximately two-thirds down the length of the femoral upright 82. That is, the fulcrum 295 is positioned about ten centimeters above the knee and the pressure point 294 is spaced about five centimeters below the perineum, or eighteen centimeters above the fulcrum. This provides a 1.8:1 mechanical advantage between the anterior force 301 applied at the upper end 308 of the lever system and the resulting posterior directed force 302 at lower end 309. Thus, the built-in posterior force 302, FIG. 17, resulting from this so-called pre-stressing by the lever arm mounting arrangement but only pre-compresses the soft tissue but, as mentioned, also applies the posterior force 302 at the lower end of the upright with a 2:1 mechanical advantage. This built-in posterior force counteracts and reduces the net effect of externally generated anterior tibial forces, as well as the anterior tibial forces which are generated by flexure of the quadriceps muscles. Specifically, when the quadriceps contract, they expand, increasing the force within the lever arm system and reducing the anterior drawer effect of the quadriceps muscles.

The third objective, achieving comfort and eliminating restrictions on movement, largely depends upon how closely the knee orthosis reflects the anatomical shapes of the leg. The casting techniques used in constructing the brace 270 provide the most anatomically accurate mold possible.

The anatomical information which is used to mold shells 271 and 272 is obtained by forming a cast over the leg and thigh using several layers of quick-setting plaster strips such as Johnson & Johnson specialist-type plaster strips. The cast is then removed from the leg and used to form the shells 271 and 272 using the vacuum mold process. During the casting procedure, before the plaster can set, the plaster can be precisely contoured by hand to the critical areas of the leg and the thigh such as, for example, the anterior surfaces of the epicondyles 77 where the adductor and tensor fascia lata tendons tract, and the hamstring muscles where the tendons for the semitendenosis 287S and the semimembranosis 287S and the biceps femoris 287B tract at the rear or posterior of the thigh. The individual reliefs 287S and 287B accommodate for the hamstring tendons, tensor fascia lata, and adductor tendons. The shapes of the quadriceps muscles are duplicated to relieve restriction on muscle contraction, especially on the vastus medius and vastus lateral. A relief 288 is also created around the fibural head to eliminate possible pressure on the peroneal nerve and potential peroneal nerve palsy. The result of this special attention to casting is an orthosis that fully achieves the objectives of comfort and non-restrictiveness.

Finally, the elastic band 278 that spans the distal posterior gastrocnemius, when tightened, effectively counters the anterior inertial force generated by the orthosis at the terminal swing point of the leg. Elastic can be used here, since the magnitude of the orthosis inertia is small. Also, an optimum limitation on extension is individually built into each orthosis 70, 170 or 270 through adjustment of the variable stops of joints 86 during fabrication.

In short, in addition to achieving the anterior-posterior medial, lateral and rotary stability and the excellent suspension characteristics which are provided by braces 70 and 170, the brace 270 provides even better anterior tibial force absorption and transfer characteristics. That is, the brace 270 incorporates an improved four point suspension system along with soft tissue compression, a lever arm construction and a closely contoured anatomical fit. These structural features cooperatively function to meet the objectives of replicating and supplementing (exceeding) the function of the anterior cruciate ligament, both against external anterior tibial forces and also against internally generated anterior tibial forces, and provides these characteristics in a comfortable, non-restrictive design. Thus, with respect to the anterior cruciate ligament, the orthosis 270 serves all of the three critical purposes: prevention of injury to the anterior cruciate ligament, stabilization of knees with a weak or injured anterior cruciate ligament, and prevention of further injury to secondary structures when the anterior cruciate ligament has been torn or injured or otherwise attenuated.

As shown in FIGS. 13 and 16, a flexible cover 289 may be applied to the joints 86. Also, an undergarment 291 of neoprene or other suitable material may be worn under the brace to provide additional suspension.

Summary and Discussion of Advantages

The knee orthosis 270 incorporates and integrates concepts of biomechanics, materials technology, and patient comfort. Its design considers control of abnormal anterior drawer with an understanding of the large magnitude of potential forces and the small quantity of allowable movement. The orthosis 270 employes a four point-pressure system which incorporates a lever-arm principle with mechanical advantage to stabilize against anterior joint motion.

The femoral shell 272 is one key to stabilization of the joints in resisting anterior joint motion. The posterior femoral section is placed ten centimeters above the knee center and a pad is placed on the superior anterior thigh five centimeters below the perineum. This placement results in an eighteencentimer distance to the posterior femoral section, on the average, creating a lever-arm system with an 18:10 mechanical advantage to stabilize the joint location.

The posterior femoral section 287 is crucial to minimizing anterior joint motion. The wide solid band 287 disperses force over a large surface area, increasing comfort and allowing greater pressure to be applied to the soft tissue area. The tendons of the biceps femoris and semitendinosus are thus allowed unrestricted motion during activity. The pressure is applied to the bellies of these hamstring muscles. The position of these anatomical structures is located at the time of casting, since there is a different relationship of the sizes of these two muscle masses for each individual. A substantial degree of comfort is attained.

The femoral shell 272 of the orthosis 270 controls anterior joint motion to within several millimeters under large under larger forces, by creating soft tissue compression prior to anterior tibial stress. The orthosis 270 accomplishes this through pre-stressing of the femoral shell. When the controls strap 299 on the superior thigh are tightened, some degree of soft tissue compression is created in the posterior thigh. When anterior joint motion occurs, the soft tissue is already compressed and anterior motion of the tibia is minimized.

The pre-stressing of the femoral shell 272 also limits full extension, since there is less soft-tissue imbedding. Another benefit of the femoral design: since it fits the entire thigh precisely, it resists motion which would move it out of alignment. This provides resistance of tibial rotation of any single degree of flexion, a secondary function of the intact ACL. Still another advantage of the femoral lever-arm system: when the quadriceps contract, they expand, increasing the force within the lever-arm system and reducing the anterior drawer effect of the quadriceps muscle.

A fourth point of pressure is established in the distal posterior gastrocnemius area through the use of an elastic band to resist orthosis inertia at terminal swing. Elastic can be used here since the magnitude of orthosis inertia is very small.

Suspension is a significant problem in the design of knee orthoses. The orthosis 270 incorporates two suspension centers 77 on the femoral condyle where there is minial tendon motion during activity. Indentations are created just anterior to the epicondyles of the adductor tendon group insertion, and just anterior to the tendon tract of the iliotibial band. This feature assists in resisting gravitational forces that cause digital migration of the orthosis.

The combination of light weight, freedom of movement and stabilization provided by the preferred embodiment 270 of my knee stabilizer or brace make it suitable for both preventive and remedial use. To give only one illustration of the value of such preventive use, in the National Football League, approximately 60 percent of injuries involve the knee. This means during the 1983 season perhaps five to seven of the fourteen linemen on each team will have suffered disabling knee injuries. This figure could be substantially reduced by the preventive use of an effective knee stabilizer.

For remedial use to protect against further aggravation of existing injuries and instabilities, the thickness and other dimensions can be tailored as required by the orthotics specialists to fit individual needs. In addition, in applications requiring very great strength and stability, albeit at the sacrifice of slightly greater weight, a material such as stainless steel can be used for the band system. One potential use which might require this substitution is mountain climbing, where safety considerations are paramount and repair or replacement may not be available.

Having thus described the knee stabilizer which embodies the principles of my invention, and specific examples of its use, the invention which I claim is:

1. A knee stabilizer for stabilizing medial-lateral, rotary, and posterior-anterior forces, including forces having an anterior tibial component, comprising:
    (a) a closed band system for surrounding the leg and thigh of a wearer, comprising a pair of medial and lateral femur uprights, a transverse posterior band connecting between the pair of femural uprights, a pair of medial and lateral tibial uprights, a transverse anterior band connecting between the pair of tibial uprights, and joint means pivotally connecting said two pair of uprights;
    (b) an anterior tibial shell comprising an anterior section mounted to said transverse tibial band adjacent the knee and thereby defining a first pressure point, said anterior section being connected between a medial section and a lateral section mounted, respectively, to said medial tibia upright and said lateral upright, said medial and lateral sections defining a posterior opening therebetween, strap means for spanning the posterior opening to cinch the shell against the wearer's leg and said tibial shell being shaped to closely fit the associated leg section, whereby said anterior tibial shell absorbs anterior tibial force components at said first pressure point and transmits the force via said tibia uprights to said femur uprights;
    (c) a posterior femural shell comprising a posterior section mounted to said transverse femur band proximate the knee and thereby defining a second pressure point, said posterior section spanning between a medial section of the femur shell and a lateral section thereof, said medial and lateral sections being mounted, respectively, to said medial femural upright and said lateral femural upright and defining an anterior opening, said femural shell being shaped to closely fit the associated thigh section and strap means spanning the upper anterior opening and spaced vertically above said posterior femural band for cinching the femural shell to the wearer's thigh, whereby the force transmitted to said femur uprights is transmitted via said second pressure point to said femur; and
    (d) said pair of femur uprights defining a lever pivotally positioned on the thigh at a fulcrum defined by said posterior femural band the posterior femural shell section such that cinching the femural shell anterior strap means pivots the upper end of said lever anteriorly about said fulcrum, thereby producing a rearwardly-directed force at the lower end of said lever for counteracting anterior tibial forces.

2. The knee stabilizer of claim 1 further comprising strap means adapted for cinching the upper section of the tibial shell to said leg adjacent the knee.

3. The knee stabilizer of claim 1, said posterior section of the femural shell comprising two protruding relief sections and an intervening recession closely approximating the outline of the biceps femoris tendons and the semitendenosis tendons and the intervening soft tissue above the back of the knee, such that cinching the femur strap means pre-compresses the soft tissue on the muscle bellies against the femur to facilitate the transfer of said anterior tibial force component from the second pressure point through the compressed soft tissue to the femur.

4. The knee stabilizer of claim 1 wherein said femur strap means comprises an anterior quadriceps pad shaped for fitting within said anterior opening of said posterior femural shell and against the quadriceps muscles for facilitating cinching of the femural shell to the wearer's thigh.

5. The knee stabilizer of claims 1, 3 or 4 wherein the posterior femural shell further includes a pair of tabs positioned on opposite sides of the patella between the patella and the femural epicondyles for preventing the knee stabilizer from slipping downward against the knee and enhancing rotatory stability.

6. A knee stabilizer for stabilizing medial-lateral, rotatory, and posterior-anterior forces, including forces having an anterior tibial component, and thereby suppressing displacement of the tibia relative to the femur, comprising:
  (a) a closed rigid band system comprising (1) a femur band system including a pair of femur uprights extending one on the lateral side of the thigh and one on the medial side of the thigh above the knee, and a transverse band connected between said femur uprights at the posterior of the femur proximate the knee, said femur uprights defining a lever pivotally positioned on the leg at a fulcrum defined by said rear femur band and having an upper lever section extending above the fulcrum and a lower lever section extending below the fulcrum, the length of the upper lever section relative to the lower lever section providing a mechanical advantage $\geq 1:1$ and (2) a tibia band system including a pair of tibia uprights extending one on the lateral side of the leg and one on the medial side of the leg below the knee pivotally connected respectively to said lateral and medial femur uprights adjacent the knee, and a transverse band connected between said tibia uprights at the anterior side of the leg proximate the knee;
  (b) an anterior tibial shell having elongated medial and lateral sections defining a rear opening therebetween and a relatively short upper anterior section proximate the knee spanning the distance between the medial and lateral sections, said anterior, medial and lateral sections being shaped to closely fit the leg of a selected wearer and being mounted, respectively, to said anterior band, said medial upright and said lateral upright of said tibia band system;
  (c) a posterior femural shell having elongated medial and lateral sections defining an anterior opening therebetween and a relatively short lower posterior section proximate the knee spanning the distance between the medial and lateral sections; said posterior, medial and lateral sections being mounted, respectively, to said posterior femur band, said medial upright and said lateral upright of said femur band system; and said posterior, medial and lateral sections being shaped to closely fit the thigh of a selected wearer, including said posterior section comprising, proximate the knee, two protruding regions and an intervening depressed region closely approximating the outline of the biceps femoris muscle and the semitendenosis muscle and the intervening soft tissue above the back of the knee;
  (d) an anterior quadriceps pad shaped for fitting within said anterior opening of said posterior femural shell; and
  (e) strap means adapted for adjustably cinching the anterior quadriceps pad to the femural shell to pivot the upper end of said lever anteriorly about said fulcrum, locking said femural shell to the thigh, thereby (1) producing a rearward-directed force at the lower end of said lever for counteracting anterior tibial force components and (2) compressing the soft tissue against the femur;
  (f) whereby, during application of a force having an anterior tibial component to the leg of the wearer, the anterior tibial section of the tibial shell transmits the anterior tibial force component to the posterior femural section of the femural shell and through the compressed tissue to the femur for limiting displacmeent of the tibia relative to the femur.

7. The knee stabilizer of claim 6, wherein the conformal, rigid posterior femural shell further includes a pair of tabs positioned on opposite sides of the patella between the patella and the femural epicondyles for preventing the knee stabilizer from sliding downward against the knee and for enhancing rotary stability.

8. The knee stabilizer of claims 1, 6 or 7 wherein the length of the upper lever section above the fulcrum relative to that of the lower lever section beneath the fulcrum provides a mechanical advantage of about 2:1.

9. A knee stabilizer, comprising
  an elongated relatively rigid anterior tibial shell substantially conformed to the leg of a wearer including the region adjacent the knee and defining a posterior opening;
  an elongated relatively rigid posterior femural shell substantially conformed to the thigh of the wearer including the region adjacent the knee and defining an anterior opening;
  the femural shell forming a first posterior pressure section, and further comprising relatively rigid strap means spanning the anterior opening at the superior border thereof and including a rigid anterior femural plate for providing a second pressure section above the first pressure section;
  a substantially closed rigid band system comprising: a pair of uprights extending one on the lateral side of the knee and one on the medial side of the knee and rigidly connecting the tibial and femural shells, each upright having a pivotal construction proximate the knee for substantially tracking flexion of the knee; a femural band section attached to the uprights on opposite sides of the femural shell and spanning the posterior side of that shell proximate the first pressure section; and a tibial band section attached to the uprights on opposite sides of the tibial shell and spanning the anterior side of that shell; and
  the tibial shell forming a third superior anterior tibial pressure section adjacent the knee and further including strap means spanning the posterior tibial shell opening for providing a fourth pressure section proximate the distal border of said shell below the third pressure section; whereby
  the four pressure sections provide a stable, four-point pressure system for restraining rotation and displacement of the knee.

* * * * *